United States Patent
Vago

(10) Patent No.: US 7,393,323 B2
(45) Date of Patent: Jul. 1, 2008

(54) METHOD AND DEVICE FOR SUBAQUEOUS ULTRASONIC IRRADIATION OF LIVING TISSUE

(76) Inventor: Robert Vago, 1196 Mallard Marsh Dr., Osprey, FL (US) 34229

( * ) Notice: Subject to any disclaimer, the term of this patent is extended or adjusted under 35 U.S.C. 154(b) by 197 days.

(21) Appl. No.: 11/042,607

(22) Filed: Jan. 25, 2005

(65) Prior Publication Data

US 2007/0167983 A1   Jul. 19, 2007

Related U.S. Application Data

(63) Continuation-in-part of application No. 10/676,061, filed on Oct. 1, 2003.

(51) Int. Cl.
*A61B 8/00* (2006.01)

(52) U.S. Cl. .............. 600/437; 601/2; 601/3; 601/4

(58) Field of Classification Search ......... 601/2–4; 600/437
See application file for complete search history.

(56) References Cited

U.S. PATENT DOCUMENTS

| | | |
|---|---|---|
| RE31,779 E | 12/1984 | Alliger |
| 4,942,868 A | 7/1990 | Vago |
| 5,048,520 A | 9/1991 | Vago |
| 5,178,134 A | 1/1993 | Vago |
| 5,305,737 A | 4/1994 | Vago |
| 5,523,058 A | 6/1996 | Umemura et al. |
| 5,665,141 A | 9/1997 | Vago |
| 5,694,936 A * | 12/1997 | Fujimoto et al. ............ 600/439 |
| 6,036,644 A | 3/2000 | Schutt |
| 6,206,843 B1 | 3/2001 | Iger et al. |
| 6,382,134 B1 | 5/2002 | Gruenberg et al. |
| 6,395,096 B1 * | 5/2002 | Madanshetty ................. 134/1 |
| 6,476,622 B1 | 11/2002 | Robinson, Jr. |

(Continued)

FOREIGN PATENT DOCUMENTS

WO   WO 2006/017561   2/2006

OTHER PUBLICATIONS

Scherba, G et. al; Quantitative Assessment of the Germicidal Eficacy of Ultrasonic Energy; 1991; American Society for Microbiology; pp. 2079-2084.

(Continued)

*Primary Examiner*—Brian L. Casler
*Assistant Examiner*—Baisakhi Roy
(74) *Attorney, Agent, or Firm*—Buchanan Ingersoll & Rooney PC

(57) ABSTRACT

Applicable to humans, animals and fish, a method for injecting thoroughly diffused ambient air or disinfectant into water prior to its delivery into a therapy tank plus an underwater PZT probe transmission of separate stable and transient cavitation signals from which a microcomputer determines, 1) the average number of transducer generated sinoidal equal amplitude alternating compression and rarefaction ultrasonic acoustic pressure waves cycles necessary to create inertial and/or transient cavitation and the required number of rectified sinoidal equal amplitude ultrasonic compression acoustic pressure waves necessary to suppress the inertial/transient cavitation and thereby maintain stable cavitation for cleaning and open-wound therapy treatment for 15-minutes, (or greater) time periods and 2) the necessary dilution of water and disinfectant and its activation by dual-mode transient cavitation to kill the pathogens shed by the "patient" following "patient" cleaning or wound-therapy treatment.

5 Claims, 8 Drawing Sheets

U.S. PATENT DOCUMENTS

| | | | |
|---|---|---|---|
| 6,719,449 | B1* | 4/2004 | Laugharn et al. ............ 366/127 |
| 2004/0049134 | A1* | 3/2004 | Tosaya et al. .................. 601/2 |
| 2005/0017599 | A1* | 1/2005 | Puskas ....................... 310/317 |
| 2005/0038361 | A1 | 2/2005 | Zhong et al. |
| 2005/0075587 | A1 | 4/2005 | Vago |
| 2005/0143638 | A1 | 6/2005 | Johnson et al. |
| 2006/0009693 | A1 | 1/2006 | Hanover et al. |
| 2006/0009696 | A1 | 1/2006 | Hanover et al. |
| 2006/0021642 | A1 | 2/2006 | Sliwa, Jr. et al. |
| 2006/0158956 | A1 | 7/2006 | Laugharn, Jr. et al. |
| 2007/0032828 | A1 | 2/2007 | Vago |
| 2007/0167880 | A1 | 7/2007 | Vago |

OTHER PUBLICATIONS

O'Brien, Willaim D. et. al.; Mouse Lung Damage from Exposure to 30kHz Ultrasound; 1994; Ultrasound in Medicine & Biology; pp. 1-24.

O'Brien, William D, et. al.; Comparison of Mouse and Rabbit Lung Damage Exposure to 30 kHz Ultrasound; 1993, Ultrasound in Medicine & Biology, vol. 20, No. 3; pp. 299-307.

O'Brien, William D. et. al.; Rabbit and Pig Lung Damage Comparison From Exposure to Continuous Wave 30 kHz Ultrasound; 1995; Ultrasound in Medicine & Biology, Vol. 22, No. 3; pp. 345-353.

Graph, Watts/cm2 vs. Frequency—mHz; Graph Modified From Esche, 1952.

Graph, Cavitation Energy vs. Viscosity, poise, No Author.

Brennen, Christopher-Earls; Quality Control of Disinfection in Ultrasonic Baths; 1995; Oxford University Press; Chapters 1-4.

Scientific American; February 1989; p. 84.

Helfrich, Louis A. et al.; Fish Farming in Recirculating Aquaculture Systems; Department of Fisheries and Wildlife Sciences, Virginia Tech; pp. 1-15.

Evaluation of Recirculating Aquaculture Systems; Oct. 1997; Minnesota Department of Agriculture and the University of Minnesota; pp. 1-33.

Kenneth S. Suslick "The Chemical and Physical Effects of Ultrasound"; Summary of Sonochemistry and Sonoluminescence, Research Group Chemistry; pp. 1-10; 2006.

USPTO Search ABST/(Ammonia and Nitrification); pp. 1-2.

70 pages of Google Search (Ammonia and Nitrification).

Philip Lymbery "The Welfare of Farmed Fish"; May 1992; pp. 1-27.

K.F. Graff "A History of Ultrasonics"; Chapter 1 of "Physical Acoustics"; vol. 15, Mason and Thurston; Academic Press; 1981.

National Academy Press; "Long Range Options: Advanced Method for Handling Liquid Waste"; 1996; pp. 1-8.

James B. Duncan, Ph.D "Bonneville Power Administration FY 2001 Innovative Project Proposal Review"; 2001; pp. 1-8.

Dana Stone "Dealing With a Toxic Threat"; News in Engineering, The Ohio State University College of Engineering; vol. 71, No. 3; Dec. 1999, pp. 1-3.

Steven Vagle "On the Impact of Underwater Pile-Driving Noise on Marine Life"; Ocean Science and Productivity Division; Institute of Ocean Sciences; DFO/Pacific; Feb. 2003; pp. 1-41.

International Search Report issued in corresponding PCT application, dated Nov. 14, 2005.

International Search Report issued in corresponding PCT application, dated Aug. 15, 2006.

H. Schöne et al.; "Quality Control of Disinfection in Ultrasonic Baths"; TU Hamburg-Harburg Reports on Sanitary Engineering 35; 2002; Ultrasound in Environmental Engineering II, pp. 1-8.

* cited by examiner

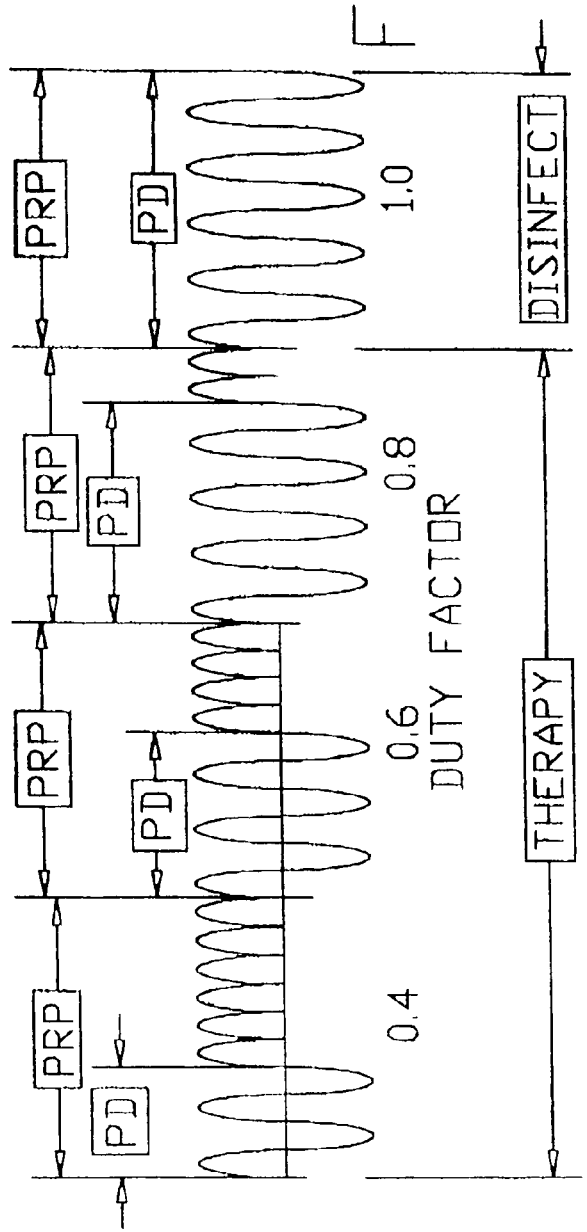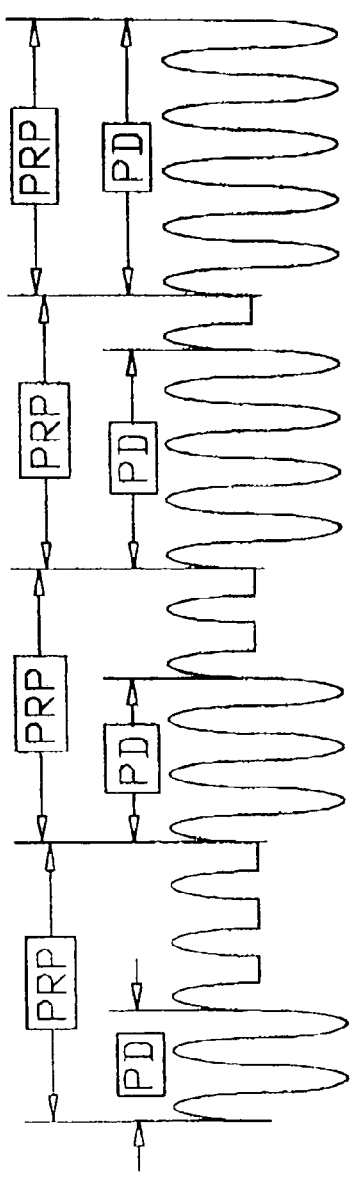

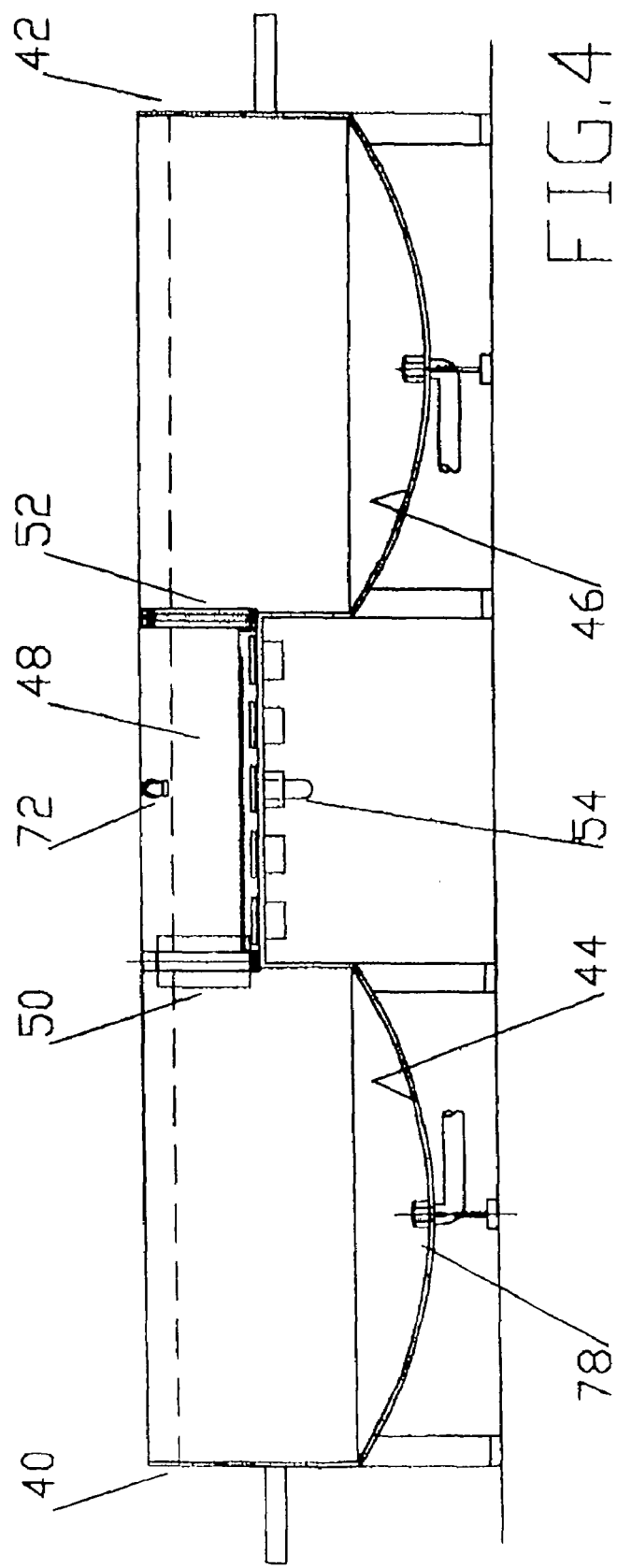

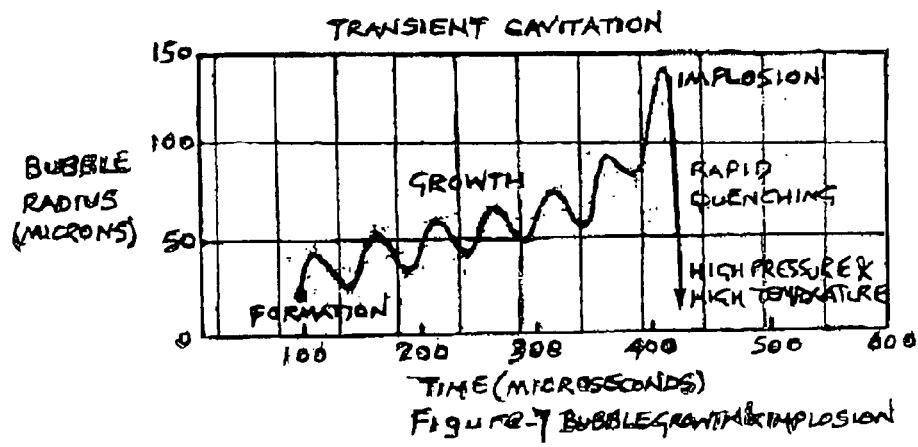
Figure-7 Bubble Growth & Implosion
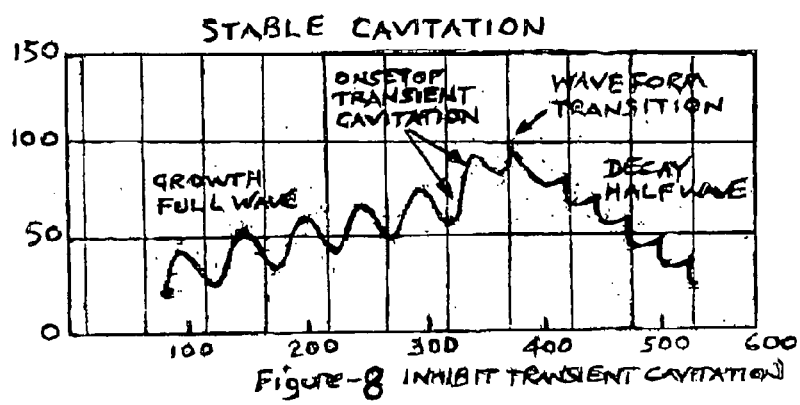
Figure-8 Inhibit Transient Cavitation
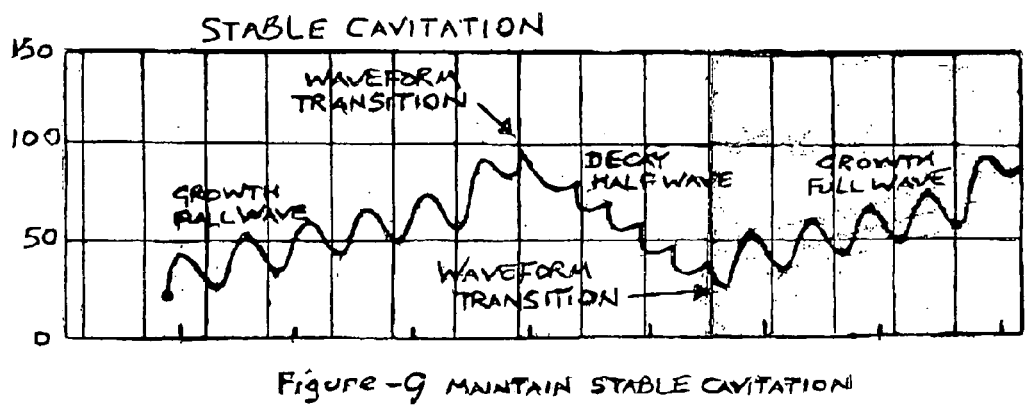
Figure-9 Maintain Stable Cavitation

METHOD AND DEVICE FOR SUBAQUEOUS ULTRASONIC IRRADIATION OF LIVING TISSUE

CROSS-REFERENCE TO RELATED APPLICATION

This application is a continuation-in-part of application Ser. No. 10/676,061 filed Oct. 1, 2003.

FIELD OF THE INVENTION

This invention relates generally to a method and an associated device or apparatus for treating living tissue with ultrasonic wave energy. More specifically, this invention relates to a method and to an associated device or apparatus for irradiating living tissue disposed in water with low-frequency, low-intensity ultrasound. The tissue may be human or, more broadly, land-animal tissue and the water may be tapwater, or the tissue may be fish tissue disposed in tapwater, brackish or saline water. Even more particularly, this invention relates to such a method and to an associated apparatus for ultrasonically treating various wound types such as skin lesions, fungus infections, inflammation, decubital and venous ulcers and other surface-tissue injuries such as lacerations and local edema.

This invention also relates to an associated method for cleaning and sanitizing tanks and water contained therein.

BACKGROUND OF THE INVENTION

In the early 1990's, the present inventor introduced a low-frequency, low-intensity ultrasound device ("Hydrosound") to effect microscopic cleaning of nursing-home patients during their weekly bathing-cycle. The preferred ultrasonic center frequency was 30 kHz and the maximum acoustic intensity was limited to 3 W/cm2, spatial peak temporal peak (SPTP). The 30 kHz center frequency was swept between 29 and 31 kHz at a rate of 120 Hz to avoid acoustic standing waves within the bathtub.

Ultrasonic human patient cleaning devices are known from U.S. Pat. No. 4,942,868, U.S. Pat. No. 5,048,520, U.S. Pat. No. 5,178,134, and U.S. Pat. No. 5,305,737. Subaqueous human application of the high frequency therapy devices is described in "CLINICS IN DIAGNOSTIC ULTRASOUND 16, edited by Wesley L. Nyborg, Marvin C. Ziskin—Section 11, Therapeutic Applications of Ultrasound, Mary Dyson.

Over the past ten years, thousands upon thousands of subaqueous exposures have demonstrated the overall safety of these ultrasonic exposure parameters for full-immersion cleaning of human patients having intact tissue with no open wounds. The only use-prohibition of the low-frequency, low-intensity ultrasound device was for wound therapy because at a frequency of 30 kHz and average acoustic intensity of more than 0.5 W/cm2 (SPTP), the device produced both inertial and transient cavitation events. Inertial or transient cavitation that occurred within 15 cm of the cleaning device's transducer demonstrated that this version of an ultrasonic cleaning modality could damage open wounds. Nevertheless, accepting this limitation, the FDA listed the low-frequency, low-intensity ultrasound device as a medical device equivalent to hydromassage or whirlpool devices but suitable for only cleaning human patients who have intact tissue without the presence of open wounds.

High-intensity ultrasound (not appropriate to this invention) can expand a bubble so rapidly during a negative-pressure cycle that the bubble collapses before it has a chance to shrink during the positive-pressure cycle. At high intensity, therefore, bubbles can grow rapidly in the course of one cycle of sound to the state of inertial cavitation collapse.

In what is known as Rectified Mass Diffusion, a bubble's size oscillates in phase with the acoustic pressure expansion (rarefaction) and compression cycles. The surface area of a bubble produced by ultrasound pressure is slightly greater during rarefaction than in compression cycles. Since the amount of gas that diffuses in or out of the bubble depends on the bubble's surface area and skin thickness, diffusion into the bubble during rarefaction cycles will be slightly greater than diffusion out during compression cycles. For each cycle of sound, the bubble expands a little more than it shrinks. Over many cycles the size of bubbles will grow slowly. With Rectified Mass Diffusion, the growing bubble can eventually reach applied frequency resonant size where it will most efficiently absorb energy from the ultrasound.

At 30 kHz, for example, the resonant bubble diameter is 100 microns while the critical bubble size, where the bubble can no longer absorb acoustic energy, is roughly 120 microns in diameter. After reaching resonant size, critical bubble size can be attained in a few more cycles of sound. When this occurs, liquid inertial force will rush into the bubble and implode it. Thus, within a few microns radius, the resulting implosion generates temperatures of thousands of degrees Kelvin and increases in pressure of thousands of atmospheres. This implosion phenomena is known as inertial or transient cavitation.

Also, when a bubble reaches a critical radius Rc at the same time that Blake's critical threshold pressure is reached, unstable bubble growth and therefore transient cavitation occur, with bubble collapse results similar to inertial cavitation. However, this particular phenomenon is subject to there being sufficient time in each pressure cycle to permit bubble growth. This is determined by the relationship between the radian frequency w of the imposed oscillations and the natural frequency wN of the bubble at its current size. If the radian frequency w is much less than the natural frequency wN then the liquid inertia is relatively unimportant in the bubble dynamics and Blake's threshold pressure criteria will hold and transient cavitation will ensue. On the other hand, if the radian frequency w is much greater than the natural frequency wN, the issue will involve the dynamics of bubble growth since its inertia will determine the size of bubble perturbations.

Inertial or transient cavitation (bubble) phenomena are manifested through the dynamic interaction of many diverse physical parameters, including the relationship between the frequency w of the imposed oscillations and the natural frequency wN of the bubble, the relationship between the pressure oscillation amplitude and the mean pressure, and whether the bubble is predominantly vapor filled or gas filled. Stable oscillations are more likely with predominantly gas filled bubbles, while bubbles that contain mostly vapor will more readily exhibit transient cavitation. Other variables that have a bearing are bubble temperature, thermal damping, water purity, surface tension, viscosity, viscous damping and radiation damping.

The probability that bubbles will oscillate stably or deteriorate into inertial or transient cavitation can be forecast mathematically if appropriate values are assigned to the above variables. Such mathematical analyses and treatises have value only post-mortem or in situations where water quality and temperature can be formulated before ultrasonic irradiation of an aqueous solution.

Unfortunately, to effect cavitation control in most patient treatment environments, water quality and its temperature control have to be viewed as an amorphous mass whose critical second-order parameters are not known and cannot be formulated beforehand. Only through experimentation can the cavitation tendency of this amorphous mass be established and only by experiment can the required ratio be determined between positive and rarefaction pressure cycles needed to predictably extend the time before a cavitation bubble implodes. Fortunately, the resulting states of cavitation from such manipulations can be determined by detecting the different acoustic pressure emission from stable and inertial/transient cavitation.

On the assumption that a human patient cleaning device would only be used for patients having intact tissue without open-wounds, it was sufficient to lower its applied ultrasonic intensity until occasional tingly-sensation events from transient cavitation in the vicinity of the patient, could be tolerated by the epidermis protected corium.

As implied above, there is a need for an ultrasound treatment device for open-wound therapy, where the body's external protective covering has broken down. On the assumption that low-frequency, low-intensity ultrasound device would only be used for patients having intact tissue, without the presence of open-wounds, standard hospital whirlpool disinfection procedures used for bathtub-cleaning after patient bathing have been judged sufficient. However, where the low-frequency, low-intensity ultrasound device is to be used with patients or subjects having open wounds, it will be critical for it to incorporate an automatic therapy tank decontamination means for killing shed pathogens between patients or subjects experiencing sonic open-wound treatments.

It is well-understood by medical-researchers that the biological basis of ultrasonic non-thermal therapy for beneficial cellular, tissue changes and wound healing depends on the presence of stable cavitation and associated microstreaming without the presence of inertial or transient cavitation. They also agree that the gas bubbles involved in transient/inertial cavitation undergo irregular oscillations and then implode, producing increases in temperature of thousands of degrees Kelvin and increases in pressure of thousands of atmospheres, localized in regions of only a few microns radius. They also recognize that any live cells exposed to such conditions would clearly be destroyed.

Side by side experiments on humans have shown that at ultrasonically treated wound sites there is an increase in total area of the blood vessels in the sections examined for both low and high frequency irradiation. There were more endothelial cells present following kHz treatment than following mHz treatment. This was particularly clear 7-days following ultrasound treatment; similar but undocumented favorable results were obtained for animals.

Several animal trials have been published in which mice, rabbits and pigs were subjected to 30 kHz low intensity ultrasound to establish the degree to which their lung tissue was damaged at increasing score levels of acoustic pressure amplitude, (0, 2, 4, 6, 8, 10, where 0 score was no damage and 10 score was death). To establish the level of ultrasound pressure vs. lung damage, 30 kHz ultrasound was propagated through thoroughly filtered water so as to eliminate the possibility of cavitation occurring or attenuation of the applied ultrasonic pressure waves. At approximately 145 kPa for 10-minutes, (8-10 score), the lungs of all the mice involved (more than 270) experienced massive lung-hemorrhage, followed by death. Subsequently, another experiment repeated the same ultrasonic exposure but this time in the presence of ultrasonic vibrating bubbles. Two mice were exposed to lethal amounts of ultrasound, (145 kPa for 10-minutes); both mice had lung damage scores of 0. A third mouse was exposed at 200 kPa and a fourth at 240 kPa and those also had lung damage scores of 0.

Because of the ability of fish to detect very low levels acoustic pressure amplitude it is very important to appreciate that the 0 kPa score clinical condition for mice was a sham condition where no ultrasound exposure was applied. It follows that when the mice were exposed to lethal levels of acoustic pressure (in excess of 145 kPa) in the presence of stable vibrating bubbles, as established by follow-on post mortems, their clinical condition was the same as the mice who received no ultrasound exposure, i.e., "alive, no lesions in lungs; normal respiration; no blood in chest cavity. No lung tissue damage; lung septa and capillaries (blood vessels) are normal." The lung damage effect on humans, rabbits and pigs was far less than on mice; the lung is considered one of the most sensitive organs to the harmful effects of ultrasound exposure.

According to Hastings, (1990), a Sound Pressure Level (SPL) greater than 0.032 kPa is not harmful to fish. A Sound Pressure Level (SPL) greater than 1 kPa is harmful to many fish. According to Norris and Mohl, (1983), a Sound Pressure Level (SPL) greater than 266 kPa is fatal to most fish.

A problem area with recirculating tanks employed for aquaculture is reducing ammonia concentrations caused by the presence of fish faeces and un-eaten fish feed particulate matter. Currently, the problem is addressed by a combination of screen filtering for the removal of un-eaten fish feed particulates and faeces-ammonia by employing nitrifying bacteria to detoxify fish excretory matter by oxidizing faeces-ammonia and nitrites into non-toxic nitrates. These bacteria are located in either trickling filters, fluidized bed sand filters or thin film filters.

While effective in reducing the concentration of ammonia in recirculating aquaculture systems, this bio-technique has drawbacks when it becomes necessary to treat fish with chemicals or drugs. Cleaning and declogging static biofilters can also pose difficult problems. Some therapeutic chemicals and drugs used to treat fish are harmful to the nitrifying bacteria situated in these biofilters. These necessary maintenance actions can lead to an abrupt lowering of the population of these nitrifying bacteria resulting in the emergence of toxic NH3 (ammonia) concentrations and resulting fish-kills. Also it can take up to 3-months to populate these filters with nitrifying bacteria.

OBJECTS OF THE INVENTION

A general object of the present invention is to provide an improved low frequency, low-intensity ultrasound device of the above-discussed type.

A more particular object of the present invention is to provide such a device that is suitable for treatment of patients or subjects with one or more open wounds.

Yet another object of the present invention is to provide such a device with a means for effectively sterilizing the device after use for wound treatment.

Yet another object of the present invention is to provide an improved method and associated apparatus for reducing ammonia concentrations caused by the presence of fish faeces and un-eaten fish feed particulate matter in recirculating aquaculture tanks.

These and other objects of the present invention will be apparent from the drawings and descriptions herein. Although every object of the invention is attained in at least one embodiment of the invention, there is not necessarily any single embodiment of the invention in which all objects are attained.

SUMMARY OF THE INVENTION

The present invention provides methods and devices that overcome the limitations of current ultrasonic human patient cleaning devices and also current high frequency human therapy devices when these are used subaqueously in a non-thermal mode for cleaning, wound debridement, and wound-healing.

It is believed that the animal experiments described above demonstrate that the presence of ultrasonically induced stable vibrating bubbles surrounding a subaqueous immersed subject serve to attenuate the applied pressure amplitude to a level equal to 0 kPa. The present invention is based in part on this observation.

A wound treatment apparatus comprises, in accordance with the present invention, a tank, a water feed pipe extending to the tank, an electromechanical transducer in pressure-wave transmitting relationship to the tank for generating ultrasonic pressure waves in water contained in the tank, and an electrical signal generator operatively connected to the transducer for energizing same with an alternating electrical signal that is partially rectified. A controller is operatively coupled to the signal generator for controlling the amplitude of the alternating electrical signal, thereby determining intensity of the ultrasonic pressure waves produced in the tank by the transducer. The controller is operatively coupled to the signal generator also for varying a pulse repetition period of the electrical signal in inverse relationship to variation of the amplitude of the electrical signal.

In accordance with another feature of the present invention, an injector is posed along the feed pipe proximate to a barrier thereof. The barrier may be a wall of the pipe, formed, for instance, by an elbow-type bend in the feed pipe. The injector is operatively connected to a valve operatively on an upstream side for introducing air into a water stream flowing along the feed pipe. The injector may be alternately coupled to a disinfectant reservoir via a valve, whereby the injector introduces a disinfectant into a water stream flowing along the feed pipe. The injector is preferably a venturi injector.

The invention is effective in part because of the replacement of diffused vaporous-gas contained by water at ambient and hot temperatures with ambient-air gas to promote stable long-term bubble vibration within the wound therapy tank. The venturi injector provides the necessary ambient-air gas for vaporous-gas to ambient-air gas exchange capability within the therapy tank. Subaqueous therapeutic benefits are obtained from ultrasonically induced stable cavitation and microstreaming in water for a meaningful or predictable time period in part because of the use of a venturi air-injector, not a simple water degassing venturi.

The prior-art human patient cleaning devices use a venturi for water degassing purposes which favor the maintenance of vapor bubbles which are more likely than air bubbles to transform from stable into inertial or transient implosions. Lowering acoustic intensity can, at best, only lengthen the time a bubble is maintained in stable cavitation before bubble expansion inevitably and naturally progresses to the inertial or transient cavitation stage.

Bubbles expansion time, from bubble inception to collapse, is relatively short and unpredictable and because there's an absence of positive stable cavitation control the technique of reducing intensity may be potentially hazardous for wound therapy. The current practice of using pulsed ultrasound where the applied ultrasonic sound wave is turned on and off to give the bubbles time to shrink back in size is said to avoid the onset of inertial or transient cavitation. This is considered tenuous logic which ignores the effects of the large number of interacting variables which, at any instant of time, may serve to randomly vary the elapsed time from bubble inception until bubble collapse possibly causing the onset of inertial or transient cavitation to occur at, or just prior to, ultrasonic sound wave turn off whereupon the bubble will continue its growth to the point of collapse and implosion. Such a subaqueous inertial or transient cavitation control technique is open-ended, (ie, no outside control) and therefore considered too risky for use with water when open-wound "patient" therapy is involved.

In accordance with a further feature of the present invention, the controller is a microprocessor is operatively coupled to the signal generator and the tank for determining a percentage or proportion of rectification of the electrical signal to obviate or avoid inertial or transient cavitation. The microprocessor may be coupled to a sensor such as a PZT probe disposed in pressure-wave transmitting relationship with water in the tank for detecting inertial or transient cavitation in the water in the tank. The microprocessor iteratively operates the signal generator during a calibration procedure to produce a series of ultrasonic pressure waves of increasing proportion of rectified waves to full waves. The microprocessor is operatively coupled to the sensor for determining a rectified/full wave duty cycle at which inertial or transient cavitation disappears. The microprocessor is programmed to operate the signal generator to produce an electrical energization signal with the duty cycle.

Thus, the present invention provides an iterative, continuous full-wave to half-wave pressure-amplitude control rather than the current practice of lowering acoustic intensity or employing on/off pulsed ultrasound, or lowering acoustic intensity. The invention employs an iterative control design approach to the suppression of inertial and transient cavitation because, without such control, the vast majority of cavities created by even the lowest amplitude rarefactional ultrasonic pressure waves are likely to result in bubble formations that will eventually implode. In layman terms, this invention looks upon water as an amorphous mass whose propensity for initiating inertial or transient cavitation varies from tank-fill to tank-fill and from location to location since its constituents and temperature state and other parameters cannot be predicted or altered in advance of wound therapy treatment.

The signal generator may be controlled to produce an unrectified ultrasonic signal to induce transient cavitation in a predetermined mixture of water and disinfectant in the tank. In that case, means may be operatively coupled to the signal generator for sweeping a frequency of an electrical excitation signal produced by the signal generator.

Pursuant to another feature of the present invention, the microprocessor is operatively coupled to the signal generator and the tank for detecting and signaling the presence of stable and inertial or transient cavitation generated in water in the tank owing to energization of the transducer. A display may be operatively connected to the microprocessor for communicating to an operator a status of cavitation in the tank.

Where fish are to be subjected the wound treatment apparatus, the tank is advantageously one of two tanks communicating with one another via a barrier.

An ultrasonic treatment method comprises, in accordance with the present invention, feeding water to a tank, dissolving air in the water to aerate the water during the feeding thereof, disposing at least a portion of a living organism in the aerated water, and thereafter ultrasonically generating stable vibrating bubbles in the aerated water. The generating of the stable vibrating bubbles includes energizing a transducer with periods of full-wave compression and rarefaction cycles alternating with periods of rectified-wave compression pressure cycles sufficient to suppress inertial or transient cavitation for a predetermined interval. The full-wave compression and rarefaction cycles having a first amplitude or intensity and a first pulse repetition period. Subsequently the transducer is energized with periods of second full-wave compression and rarefaction cycles alternating with periods of second rectified-wave compression pressure cycles, where the second full-wave compression and rarefaction cycles have a second amplitude or intensity greater or less than the first amplitude or intensity and a second pulse repetition period respectively less or greater than the first pulse repetition period. The second rectified-wave compression pressure cycles have the second amplitude or intensity and the second pulse repetition period so that the second full-wave compression and rarefaction cycles alternating with periods of the second rectified-wave compression pressure cycles are sufficient to suppress inertial or transient cavitation for a predetermined interval.

The method may additionally comprise automatically monitoring the aerated water in the tank to detect inertial or transient cavitation. If so, the method may also comprise displaying a status of inertial of transient cavitation in the aerated water in the tank.

Pursuant to a yet another feature of the present invention, after the organism is removed from the tank, a disinfectant is delivered to the tank. Thereafter ultrasonic transient cavitation is induced in water and disinfectant contained in the tank. The inducing of the ultrasonic transient cavitation preferentially includes generating full-wave compression and rarefaction cycles at an ultrasonic frequency in the water and disinfectant in the tank. Also, the inducing of the ultrasonic transient cavitation may further include sweeping the frequency.

An ultrasonic treatment method comprises, in accordance with the present invention, disposing at least a portion of a living organism in aerated water, and thereafter ultrasonically generating stable vibrating bubbles in the aerated water for a first predetermined interval. The generating of the stable vibrating bubbles includes energizing a transducer with a first alternating electrical signal to suppress inertial or transient cavitation for the first predetermined interval, the first alternating electrical signal having a first amplitude and a first pulse repetition period. Thereafter stable vibrating bubbles are ultrasonically generated in the aerated water for a second predetermined interval, the generating of the stable vibrating bubbles during the second predetermined interval including energizing the transducer with a second alternating electrical signal to suppress inertial or transient cavitation for the second predetermined interval, where the second alternating electrical signal has a second amplitude and a second pulse repetition period, with the second pulse repetition period differing from the first pulse repetition period in inverse relationship to a variation of the second amplitude relative to the first amplitude.

As described above, the present invention provides a method and/or apparatus for periodically stimulating and then arresting cavitation bubble-growth as the means for perpetuating stable cavitation and the elimination of inertial or transient cavitation for a time period sufficient to permit completion of open wound therapy or cleaning, typically 10-15-minutes.

The present invention enables the application of ultrasonic frequency with stable cavitation, exhibiting subaqueous sub-harmonics above the threshold of normal human hearing so that the human patient does not detect the sub-harmonics through skeleton bone conduction. For treatment of farm-raised fish, this sub-harmonic emission precaution is not necessary as their frequency detection capability is far below ultrasound frequency.

The present invention contemplates injecting and then diffusing ambient air into the water supply before that water enters a bathing or wound-therapy treatment tank in order for the ambient air to displace vapor from vapor bubbles formed by cavitation in the therapy tank.

In an apparatus and method in accordance with the present invention, an attenuating blanket of stable vibrating air bubbles is generated that surrounds a patient or subject to prevent ultrasonic pressure waves from entering the "patient's" body and additionally, for the fish "patient," provision of a source of oxygen during its debridement and wound therapy.

To ensure bubble blanket intensity uniformity around the human or animal patient, one ultrasonic transducer is centrally located at the bottom of the therapy tank. For the fish subjects, since they are mobile and many may be treated at the same time, multiple transducers are mounted to the bottom of the therapy tank.

The present invention provides an alternative to the current 1-5 mHz, hand-held human therapy devices when used in the non-thermal, subaqueous mode with this invention's low frequency alternative because, when current high frequency (1-5 mHz) therapy devices are used subaqueously for non-thermal wound treatment, the water bubble cavitation attenuation blanket described above cannot be created so the applied ultrasonic pressure waves penetrate the human patient's body. There is risk, therefore, with these prior art devices of causing inertial or transient bubble cavitation events at various nucleation sites which exist within human or animal bodies.

The basic difference between the present invention and current high frequency devices used for subaqueous non-thermal human wound therapy is that this invention relies upon stable cavitation and microstreaming stimulated in the aqueous solution surrounding the patient or subject while the high frequency device assumes low-intensity ultrasound pressure waves will not cause transient cavitation to form within a subject's body.

To enable the microprocessor to distinguish between stable cavitation and inertial or transient cavitation events occurring in the contained tapwater within the wound therapy tank, the underwater detector circuitry pursuant to the present invention provides two separate signals, one that responds to harmonic "noise" (which is characteristic of stable cavitation) and the other that responds to broadband "noise" (which is characteristic of inertial or transient cavitation).

The present invention also contemplates a method for reducing ammonia concentrations caused by the presence of fish faeces and un-eaten fish feed particulate matter in recirculating aquaculture tanks. The method is based on the considerable research that has been done in the field of low frequency ultrasound with respect to cavitation bubble collapse and and that created a new scientific discipline known as the Sonochemistry of liquids. According to Suslick, Scientific American, 1989, due to the creation of very high temperatures (5500 degrees C.) and pressures (500 atmospheres), which develop as a cavitation bubble collapses, organic compounds in the vicinity will be highly degraded and inorganic compounds oxidized or reduced.

Since ammonia ($NH_4$) is an inorganic compound, its oxidation through cavitation bubble collapse will serve to detoxify fish excretory matter by converting faeces-ammonia and nitrites into non-toxic nitrates.

The present method for reducing ammonia concentrations in recirculating aquaculture tanks comprises monitoring ammonia levels in fish tank water, removing fish from at least a portion of the fish tank water to thereby isolate the portion of the fish tank water, upon detecting a predetermined ammonia concentration in the fish tank water, ultrasonically generating transient cavitation bubbles in the isolated portion of the fish tank water to oxidize ammonia therein, and subsequently mixing the ultrasonically treated portion of fish tank water with an ultrasonically untreated portion of the fish tank water.

The isolated portion of fish tank water may be directed through a screen filter, for instance, after being subjected to ultrasonic pressure waves.

While effective in reducing the concentration of ammonia in recirculating aquaculture systems, the present invention's ultrasonic (non-bio) technique exhibits none of the above drawbacks listed for bio-techniques when it becomes necessary to treat fish with chemicals or drugs including the troublesome but necessary cleaning and declogging of biofilters.

The detoxification of ammonia and carbon-dioxide removal is accomplished, pursuant to the present invention, by multi-tasking the ultrasonic generator system used for wound cleaning and therapy and placing the associated management and control procedures with the microprocessor as described in U.S. patent application Ser. No. 10/676,061. The removal of un-eaten fish feed particulate matter will be accomplished by screen filtering.

Removal of un-eaten fish feed particulate matter and oxygenation of tank water is essentially a continuous ongoing process. The detoxification of ammonia and carbon dioxide removal is periodic process dependent on their toxicity levels, as indicated by suitably placed monitors or sensors.

These control means may be manual or automatic, as preferred. When automatic, they are under the control of the microprocessor.

BRIEF DESCRIPTION OF THE DRAWINGS

FIG. 2A is a graph of a pulsed waveform used for iterative stable cavitation control in a method and apparatus in accordance with the present invention, showing a fully rectified wave portion.

FIG. 2B is a graph of another pulsed waveform used for iterative stable cavitation control in a method and apparatus in accordance with the present invention, showing a half-wave rectified wave portion.

FIG. 4 is an elevational view of the two-tank fish farm with ultrasonic therapy installation shown in FIG. 3.

FIG. 7 is a graph of bubble radius vs. time, illustrating stable cavitation degenerating into transient cavitation.

FIG. 8 is a graph of bubble radius vs. time, illustrating an interval of stable cavitation followed by a period of rectified half-wave transmission, in a method pursuant to the present invention.

FIG. 9 is a graph of bubble radius vs. time, illustrating an interval of stable cavitation followed by a period of rectified half-wave transmission, in turn followed by stable cavitation, in a method pursuant to the present invention.

DETAILED DESCRIPTION OF THE PREFERRED EMBODIMENTS

The following operational description of a wound treatment apparatus applies to human and animal configurations of the apparatus. A configuration of the apparatus for the treatment of fish need not include provision for handling disinfectant in a therapy tank but will include all other operational features plus some additional features necessary to address the needs of fish farming.

Figure 1:
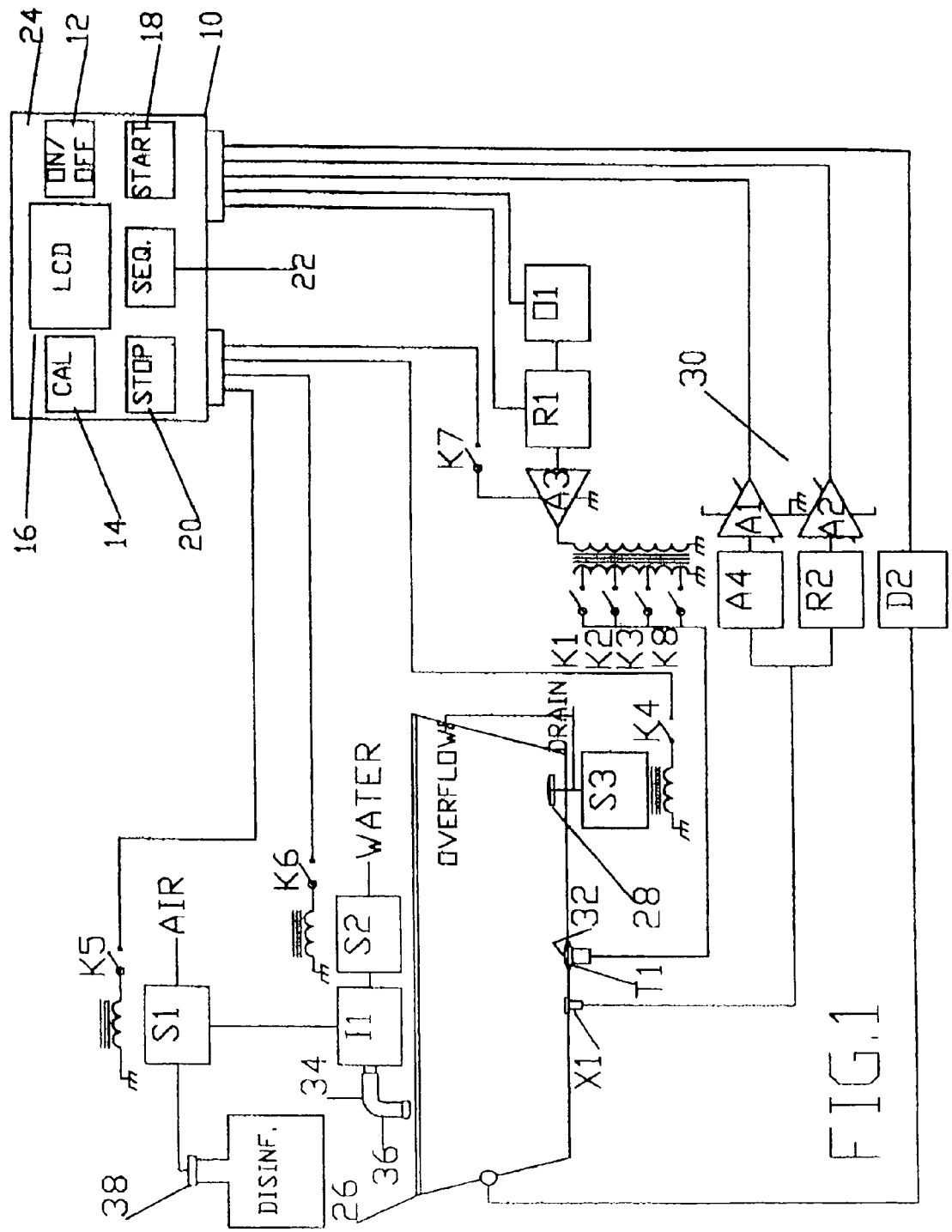
FIG. 1 is an overall system block diagram outlining functional interrelationships among three major elements of a human and land-animal debridement and wound-therapy supine treatment apparatus in accordance with the present invention.

FIG. 1 illustrates a control microcomputer or microprocessor 24 by which means an operator can cause the three processes associated with open-wound ultrasonic therapy to function, as needed. Microprocessor 24 has a control panel (not separately designated) includes an illuminated touchpad 12 for activating the wound treatment apparatus. Another illuminated touchpad 14 initiates a "one time" on-site calibration cycle. A liquid crystal display (LCD) 16 displays all relevant information and operator instructions. A further touchpad 18 is used to initiate a "start selected sequence" routine. Yet another touchpad 20 initiates a "stop selected sequence" routine. A sequencer touchpad 22 is accessed by microcomputer or microprocessor 24 to assist the operator in initiating the required operation.

The wound treatment apparatus described herein operates in either a manual or an automatic operational mode and either mode is selectable at the operator's choice.

Sequencer touchpad 22 runs the LCD 16 through a menu so the operator can make selections as required. The menu is set forth in the normal sequence of operation, i.e., therapy tank fill, wound debridement/cleaning, wound healing, decontamination/auto therapy tank drain, therapy tank drain, fish conditioning and fish excrement removal. Each of these operations, other than therapy tank fill, may be taken in the operator preferred order, e.g., if for humans and animals the operator wanted to disinfect the therapy tank before wound therapy, this is possible but the microcomputer 24 will instruct the operator not to install the patient and will empty the therapy tank at the completion of the automatic decontamination cycle time.

Before the wound treatment apparatus can be used for routine therapy treatment it must first be calibrated onsite. When a therapy tank 26 (FIG. 1) is filled the first time, the operator activates the system by depressing the illuminated "ON" touchpad 12. This activates all electronic circuits but stops ultrasound transmission to the therapy tank 26 by opening a switch K7 to disable an amplifier A3. The operator, by means of the sequencer touchpad 22 and LCD 16 selects from the menu option "THERAPY TANK FILL." Microcomputer 24 then asks the operator via LCD 16 to select "AUTO, (FILL)." After making the required selections the operator is instructed by microcomputer 24 via LCD 16 to depress the "START" touchpad 18. Microcomputer 24 closes a switch K4, which energizes a solenoid S3 and closes a drain 28. Then a switch K6 is closed, which energizes a solenoid S2 and commences aerated tub fill. The therapy tank fill components are turned off when a preset level is reached as determined by a sensor D2.

Calibration

Until microcomputer 24 has conducted its first on-site calibration, it will only respond to an instruction to fill the therapy tank 26. Microcomputer 24 will tell the operator via LCD 16 why and ask the operator to depress calibration (CAL) touchpad 14. The calibration cycle is fully automatic and operates as follows.

An initial step in an iterative control technique is to test the number of full sinusoidal cycles of equal amplitude ultrasonic compressional and rarefactional pressure waves needed to stimulate inertial or transient cavitation in water. This is accomplished by running ten discrete sets of tests of which the longest and the shortest number of cycles are discarded and the average number of cycles is calculated from the remaining eight tests.

This average number of cycles is the pulse repetition period, i.e., the time from the beginning of one pulse to the beginning of the next. There is no ultrasound "off" time in this pulse repetition period since it is made up of two different pulse types, one immediately following the other. The pulse duration (PD) is the length of time required for the first type pulse to occur and is equal to the period times the number of sinusoidal cycles in the pulse. The duty factor is the fraction of time that the first type pulse is on and consists of full sinusoidal compressional and rarefaction pressure waves. The balance of the pulse repetition period is occupied by the second pulse type, which consists of half sinusoidal (rectified) compressional pressure waves The iterative stable cavitation control technique consists essentially of decreasing the above-defined duty factor from 0.8 in increments of 0.1, for example, until the setting is reached where it takes transient cavitation 15 minutes or more to manifest itself, whereupon, the duty factor is reduced, for example, by an increment of 0.1 to provide a safety margin.

The above iterative control technique is conducted with the average time to transient cavitation calculated from the above ten discrete sets of tests corresponding to the duty factor 1.0 and using the precision microcomputer clock as the determinant for setting the trial duty factors where it takes transient cavitation 15 minutes or more and whose value and increments are adjusted from tank to tank location to suit water quality.

Upon completion of the above calibration cycle the microcomputer 24 through its LCD 16 confirms that stable cavitation is in effect. Thereafter, the calibrated ultrasound wave configuration is transmitted continuously while the 15-minute "patient" cleaning, wound debridement or wound healing therapy is in progress.

In an example of a wave configuration arrived at via the above-described iterative calibration technique, the duty factor is 0.4, with full-wave rectification, the applied frequency is 60 kHz, and the pulse repetition period (PRP) is 15 seconds. Then the number of alternate compressional and rarefaction cycles is (15×60,000×0.4)/2 or 180,000. For a duty factor of 0.6, the number of alternate compressional and rarefaction cycles is 270,000. The number of follow-on compressional half-cycles is 15×60,000×0.6 or 540,000 and, for a duty factor of 0.6, the number of alternate compressional and rarefaction cycles is 360,000.

After the 15-minute therapy period is completed, or transient cavitation is detected, the microcomputer 24 shuts down the ultrasound for a time period sufficient for cavitation to dissipate, whereafter therapy can be resumed for another 15-minute time period, and so on.

This calibration cycle is more likely a one-time event necessary upon device site installation because water quality varies widely depending on geographical location.

The final waveform resulting from this calibration at a particular location is placed into the memory of microcomputer 24 and is applied for all subsequent device activations at this particular site location.

The presence or absence of inertial or transient cavitation is determined by a signal from a PZT probe X1 (FIG. 1) situated in close proximity to a transducer T1 and in combination with an appropriately configured detection circuit 30. PZT probe X1 generates a signal fed to microcomputer 24, which manages all associated signals, system components and processes.

Operator control over microcomputer 24 is provided by a control unit 10 including LCD component 16, which are situated on or near wound treatment therapy tank 26.

Microcomputer 24 induces the energization of transducer T1 with a full-wave ultrasonic waveform alternating with a rectified alternating waveform, defined by parameters selected during the calibration process as discussed above. This ultrasound generation method suppresses inertial and transient cavitation. The system generates bubbles at the applied frequency and compresses the bubbles so that they are smaller than their resonant size at the applied frequency, thereby prolonging stable cavitation.

Because vibrating bubble-to-bubble interaction causes bubbles to assume a non-spherical shape, their vibratory response is non-sinusoidal and therefore contains harmonics and sub-harmonics of the applied frequency. A limitation of the above-discussed prior-art human patient cleaning device was the 30 kHz applied frequency because its third sub-harmonic 10 kHz, proved detectable by all immersed human patients through conduction of the 10 kHz subharmonic by their bony prominances to their inner-ear, some patients finding the noise either irritating or intolerable. For the prior human patient cleaning device, lowering the applied intensity served to decrease the amplitude of the third sub-harmonic which lowered the noise to an acceptable level in most but not all cases. This necessary lowering of intensity proved to be at the expense of cleaning process effectiveness for the patient.

The present apparatus has removed this limitation by increasing the applied frequency to 60 kHz for human and animal exposure and therefore its third sub-harmonic to 20 kHz, which is above the threshold of human hearing. The detection circuit 30 may also employ harmonics for detection of stable cavitation.

For fish treatment, the applied ultrasonic frequency is lowered to 30-kHz, because the frequency detection capability of farm-raised fish is, at the highest, in the low hundreds of Hz.

The present apparatus provides four levels of intensity, one for decontamination at more than 5 W/cm$^2$ SPTP, the second for cleaning and open-wound debridement at 3 W/cm2 SPTP (maximum), the third for wound healing at 1.5 W/cm2 SPTP (maximum), and the fourth for fish conditioning at 0.5 W/cm2 SPTP. The 30 or 60 kHz applied frequency is swept up to +/−5 kHz at 120 Hz to provide the likelihood of increased microorganism kill.

The limitation exhibited by 1-mHz-and -above hand-held therapy device is its inability at 0.1-0.5 W/cm2 intensity to stimulate any form of cavitation in the water thus enabling ultrasonic pressure waves to penetrate a human patient's body without attenuation, thereby exposing nucleation sites within the patient to cell damage and free radicals from inertial or transient cavitation. This limitation of these hand-held devices can only be removed by lowering their applied frequency and increasing the acoustic intensity of the devices. There's no better example than the 1 mHz hand-held therapy device for demonstrating that water's reaction to ultrasonic pressure waves may have unanticipated major harmful effects on the desired therapeutic clinical result and that reliance on first-order, open-ended controls to effect stable cavitation may only serve to increase the risk of cell damage due to the non-visible presence of inertial or transient cavitation within the human patient's body.

An advantageous element of the present apparatus is an ability to differentiate between occurrences of stable and inertial or transient cavitation within contained tapwater within a wound-therapy tank 26. An inertial or transient cavitation detection signal always overrides the stable cavitation detection signal so that microcomputer 24 can suppress or maintain inertial or transient cavitation depending on the required mode of operation.

The location of PZT probe X1 of detector circuit 30 is in-line with a face 32 of transducer T1 at the highest intensity within the wound-therapy tank 26. In response to a signal from PZT probe X1, microcomputer 24 displays on LCD 16 the cavitation status within the water contained within the wound-therapy tank 26 at all times during operation.

PZT probe X1 and detection circuitry 30, inter alia, overcome the limitation of prior human patient cleaning devices in their inability to detect inertial or transient cavitation and to thereby maintain stable cavitation suitable for wound-therapy.

Decontamination

The need is recognized for disinfection of a tank 26 used for ultrasound wound treatment. After completion of a wound-therapy procedure in therapy tank 26, the tank must be decontaminated from pathogens shed by the patient or subject. A number of microorganisms have been found to withstand hot-water temperatures and chemical disinfectants, which suggests that chemical means alone are not 100% effective. Also, experimental data suggests that ultrasound in the low-kilohertz frequency range is capable to some measure of inactivating certain human disease agents that may reside in water. This experimental ultrasound data states that the human pathogens tested were selected on their normal routes of infection, for example, skin or intestinal tract, or their structural similarities to such agents, which would make them likely candidates of whirlpool or hot tubs.

In an experiment, ultrasound killed within 1 hour a variable percentage of the following microorganisms: bacteria (*Pseudomonas aeruginosa, Bacillus subtilis Escherichia coli*), fungus (*Trichophyton mentagrophytes*) and viruses (feline herpes virus type 1; this sub-family also includes the human herpes viruses, herpes simplex virus types 1 and 2). This experiment concluded that 100% microorganism killing was a dose-effect dependent on time of exposure and level of ultrasound intensity but the mechanism of microorganism "kill" appeared to be inertial or transient cavitation.

This microorganism "kill" principle appeared to be the high forces and high temperatures associated with inertial or transient implosions which can disintegrate cell walls and membranes of bacteria and certain enveloped virus but only in the immediate vicinity of these micro-sized implosions. Because an apparent defense mechanism of pathogens is to gather at the antinodes of a constant frequency ultrasonic wave where the amplitude of the ultrasound pressure wave is at a minimum, the present apparatus employs a rapid frequency-sweep modality which serves to oscillate the location of the antinodes in space thereby exposing the microorganisms to an increased number of cavitation implosion events.

Experimental data reveals that ultrasonic cavitation enhances the effect of different antibiotics and disinfectants. Clearly, disinfectant plays no part in the deactivating of pathogens exposed to the high forces and temperatures created by cavitation implosion events. Reasons for the synergism of water, ultrasound and disinfectant having an apparently enhancing germicidal effect over water and disinfectant alone are largely unknown. Since experiments have demonstrated acoustic pressure waves used in conjunction with disinfectant does exhibit an increased germicidal effect, the synergism hypothesis is that like vibrating bubbles the pathogens are subjected to alternating compression and rarefaction ultrasonic pressure waves. Since the pathogen's internal contents are normally equalized in pressure corresponding to ambient pressure, in the presence of a rarefaction pressure wave an enveloped pathogen expands in size from internal pressure because of the absence of balancing external pressure. On the following ultrasonic compressional pressure wave the enveloped pathogen is squeezed to a size smaller than normal, further increasing the pressure on the inner contents. The oscillatory stress pattern on a pathogen's envelope could be repeated up to 30,000 to 60,000 times each second. It is hypothesized that these many positive to negative stress inversions may cause cell-wall fatigue which in turn creates fissures or even fractures in a cell-wall or membrane which open upon rarefaction pressure cycles, thereby exposing the microorganism's inner contents and then close shut on the compression pressure cycle.

It is also hyphothesized that if the medium surrounding the pathogen was water these stress inversions on the pathogen might be survivable for longer time-periods, but when the medium is disinfectant, as the fissures or fractures open on the rarefaction pressure cycle exposing the pathogen's inner contents to disinfectant, the following compressional pressure cycle forces the disinfectant into the cell's interior, thereby killing the cell.

The present apparatus exhibits a decontamination cycle employing a combination of water, ultrasonic pressure waves, and disinfectant in order to secure disinfection within a shorter time period than is possible with ultrasound and water alone or disinfectant alone, with the goal of taking less time to effect disinfection than current hospital procedures, which range typically from 12-30-minutes. The required disinfectant should exhibit a surface tension approaching that of water (72 dyne/cm) and a viscosity approaching that of water (0.01 poise) and exhibit germicidal action against the microorganisms listed above and those microorganisms appropriate to animals, and be non-flammable.

In fish farming applications, there is a difficulty with containing disinfectant in the ultrasonic therapy tank. Therefore disinfectant is not used to kill fish microorganisms. Instead, the necessary full ultrasonic dose effect (time and ultrasonic intensity) applicable to transient cavitation 100% microorganism kill is used.

In order to increase the spectrum of microorganism kill, it is intended that all patient germicidal cycles employ the wound therapy pulsed waveform with its duty factor set to low values (less than 0.4), sufficient to induce transient cavitation and the collapsing of very small bubbles.

Because decontamination is accomplished by the use of transient cavitation and not stable cavitation, the apparatus includes a number of patient precautionary or protection measures. The decontamination cycle is under microcomputer control, which dictates the following operational sequence.

By means of touchpads 12, 18, 22, etc., therapy tank 26 is automatically filled to preset levels and also emptied automatically (except in the case of fish). Ultrasonic decontamination cannot be accessed until wound treatment has been conducted and operator confirmation of patient or subject removal from the therapy tank 26. Microcomputer 24 determines readiness for wound treatment by noting that the wound treatment preset tank fill level and automatic water shut off is completed. After termination of the preset 15-minute wound treatment time, microcomputer 24 informs the operator via LCD 16 that therapy tank decontamination can take place and provides the necessary touchpad instructions via the LCD. The instructions include the appropriate decontamination information and an instruction requiring mandatory patient removal from the therapy tank 26 before decontamination can be initiated and requires touchpad confirmation of patient removal to be confirmed to microcomputer memory. After confirmation of patient removal, microcomputer 24 adds a specific volume and dilution of tapwater and disinfectant to the therapy tank 26 then activates ultrasonic full-wave, equal-amplitude compressional and rarefaction and half-cycle compressional pressure waves sufficient to cause transient cavitation for the preset decontamination time period after which the microcomputer automatically switches off the ultrasound. For a fish decontamination cycle, disinfectant may not be employed due to the difficulty of containing disinfectant in the ultrasonic therapy tank. During the decontamination time period, audible and visual annunciators including a flashing LCD display are active, signifying an "operator precautionary" condition.

After decontamination is completed, microcomputer 24 automatically drains tank 26 and requests via LCD 16 that the tank be rinsed with tapwater and then dried with germ-free cloths or a thermal blow drier. Microcomputer 24 disconnects the system from electrical power after a preset time period.

Microcomputer 24, using its internal precision clock, synchronizes with a 30 or 60 kHz oscillator O1 to time an interval from a closing of switches K1 and K7 and an activating of amplifier A3 to a signaling of an adjustable-gain amplifier A2 by PZT detector X1 that transient or inertial cavitation has taken place, at which time the microcomputer places the resulting time into temporary memory then repeats the process for a total of ten times before calculating the average pulse repetition period. Using the average pulse repetition period, the calibration cycle (or program) next requires microcomputer 24, using its internal precision clock, to synchronize the 30 or 60 kHz oscillator O1 with a full-wave rectifier R1 to form a 0.8 duty factor pulse-train (see FIG. 2A) and then to close switches K1 and K7 which activates amplifier A3 until PZT detector X1 signals the adjustable-gain amplifier A2 that transient or inertial cavitation has taken place, at which time the microcomputer compares the elapsed time from the activation of amplifier A3 until to the signaling by amplifier A2 that transient cavitation has occurred for the required time of 15 minutes.

Microcomputer 24 automatically resets the duty factor to a lower value and continues as described above until a duty factor value is attained that results in the required time of 15 minutes. The duty factor may be reset in increments of less than 0.1.

PZT detector X1 feeds both a 10 or 20 kHz acceptor circuit A4 and a 10 or 20 kHz rejector circuit R2 which feed an adjustable gain narrow-band sub or harmonic amplifier A1 and the adjustable-gain broadband amplifier A2 whose outputs are fed to the microprocessor. Acceptor circuit A4 and rejector circuit R2 may employ harmonics or sub-harmonics.

From the amplifiers A1 and A2 outputs the microprocessor 24 determines the required pulsed waveform needed to arrest inertial or transient cavitation for a minimum time period of 15 minutes (or other suitable time selectable by the operator).

After the required pulsed waveform has been determined, microcomputer 24 places the defining parameters of the determined pulse waveform into an internal memory. Those parameters are used thereafter for all open-wound therapy purposes at the particular installation site.

The operator can empty the therapy tank 26 either by following instructions displayed on LCD 16 or by depressing illuminated "ON" touchpad 12. Either action opens switch K4, thereby de-energizing solenoid S3 to open drain 28. Subsequently depressing the "illuminated" ON touchpad 12 removes all electrical power from the invention including touchpad illumination.

Upon completion of the onsite calibration cycle, the invention is ready for routine open-wound therapy treatment or, if required, intact tissue "patient" cleaning (see FIG. 2A) for the cleaning and therapy pulsed waveforms.

There are four intensity levels of ultrasonic transmission: (1) decontamination triggered or activated by switch K1, (2) wound debridement/cleaning, triggered or controlled by operation of a switch K2, (3) wound healing, which is triggered or activated by operation of a switch K3, and (3) fish conditioning, which is initiated by operation of a switch K8.

There are three modes of ultrasonic transmission: (1) continuous, which is reserved for the decontamination cycle, (2) pulsed at a duty factor greater than 0.4 for the decontamination cycle, and (3) pulsed for the absence of inertial or transient cavitation which is reserved for the wound debridement, wound healing and fish conditioning cycles.

Microcomputer 24 alternately enables and disables rectifier R1 using either a duty factor of less than 0.4 (enable), or 1.0 (disable) for the decontamination mode, and only enables rectifier R1 for wound debridement, wound healing and fish conditioning (see FIG. 2).

The duty factor (less than 0.4) is determined by microcomputer 24 in a fashion similar to that described above, with the criteria being the lowest duty factor that stimulates continuous transient cavitation due to a majority of compressive pressure waves that collapse very small bubbles.

During a decontamination process preferably used in connection with the treatment of humans and animals but probably not fish, microcomputer 24 holds off amplifier A3 by keeping switch K7 open until it has completed the following actions: (i) the therapy tank is filled to the preset control level detected by sensor D2, (ii) the ambient-air input normally fed through the venturi for therapy tank filling is replaced by disinfectant by closing switch K5 which energises solenoid S1, and (iii) the microcomputer clock is set to deliver the preset dilution of disinfectant necessary to effect the required sonic germicidal action based on the volume of water contained by therapy tank 26 up to its overflow port and beyond, if necessary (experiment). Microcomputer 24 then closes switch K6, which energizes solenoid S2 so that the velocity of the water supply causes a venturi I1 to suck in disinfectant until the microcomputer shuts down the water supply and disinfectant by de-energising solenoids S1 and S2. Venturi I1 is an injector posed along a feed pipe 34 proximate to a barrier formed by a wall of the pipe, for instance, at a 90-degree elbow-type bend 36 in the feed pipe. Venturi injector I1 is operatively connected to solenoid valve S1 on an upstream side for introducing air into a water stream flowing along feed pipe 34. Venturi injector I1 is alternately coupled to a disinfectant reservoir 38 via solenoid valve S1, whereby the injector introduces a disinfectant into a water stream flowing along feed pipe 34.

Microcomputer 24 then delivers 30 or 60 kHz ultrasound at an intensity in excess of 5 W/cm2 SPTP for the pre-set decontamination time period as monitored and controlled by the microcomputer clock. Upon completion of the decontamination cycle, and in the auto mode, the microcomputer opens the drain 28 by opening switch K4 which de-energizes solenoid S3. Microcomputer 24 then follows its shut down procedures prior to disconnecting from electrical power.

The present apparatus as used for treating fish utilizes existing technology for general water-quality maintenance in fish holding tanks 40 and 42 (FIGS. 3 and 4) such as the requisite number of sequential rotating water jets (not shown) situated on a tank's bottom surface 44, 46 necessary to sweep all fish excrement from the tank bottom surfaces into a drain return 78 situated at the lowest point on the tank bottom 44, 46. The fish excrement particulate is then sucked into and is retained by filters (which are removable and cleanable) by means of a bi-directional pump/motor assembly 58 including a motor 100, a pump 102, and pair of filters 104 and 106

Figure 5:
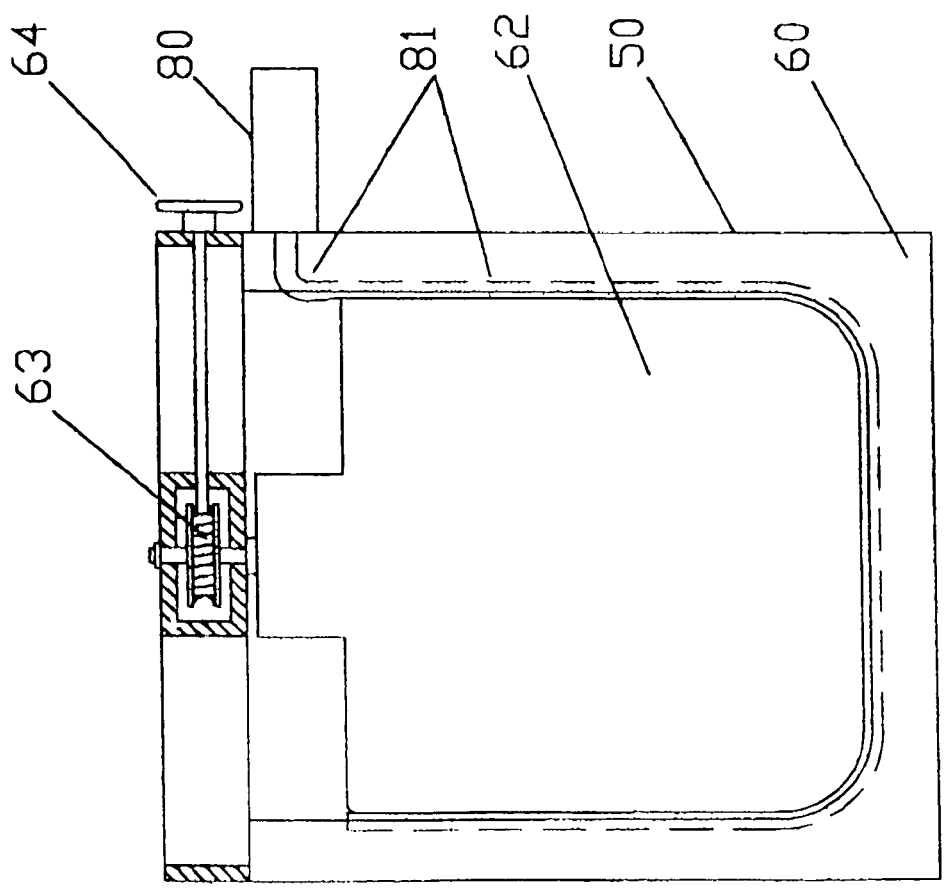
FIG. 5 is a schematic front elevational view of a louvered barrier shown in FIGS. 3 and 5.
Figure 10:
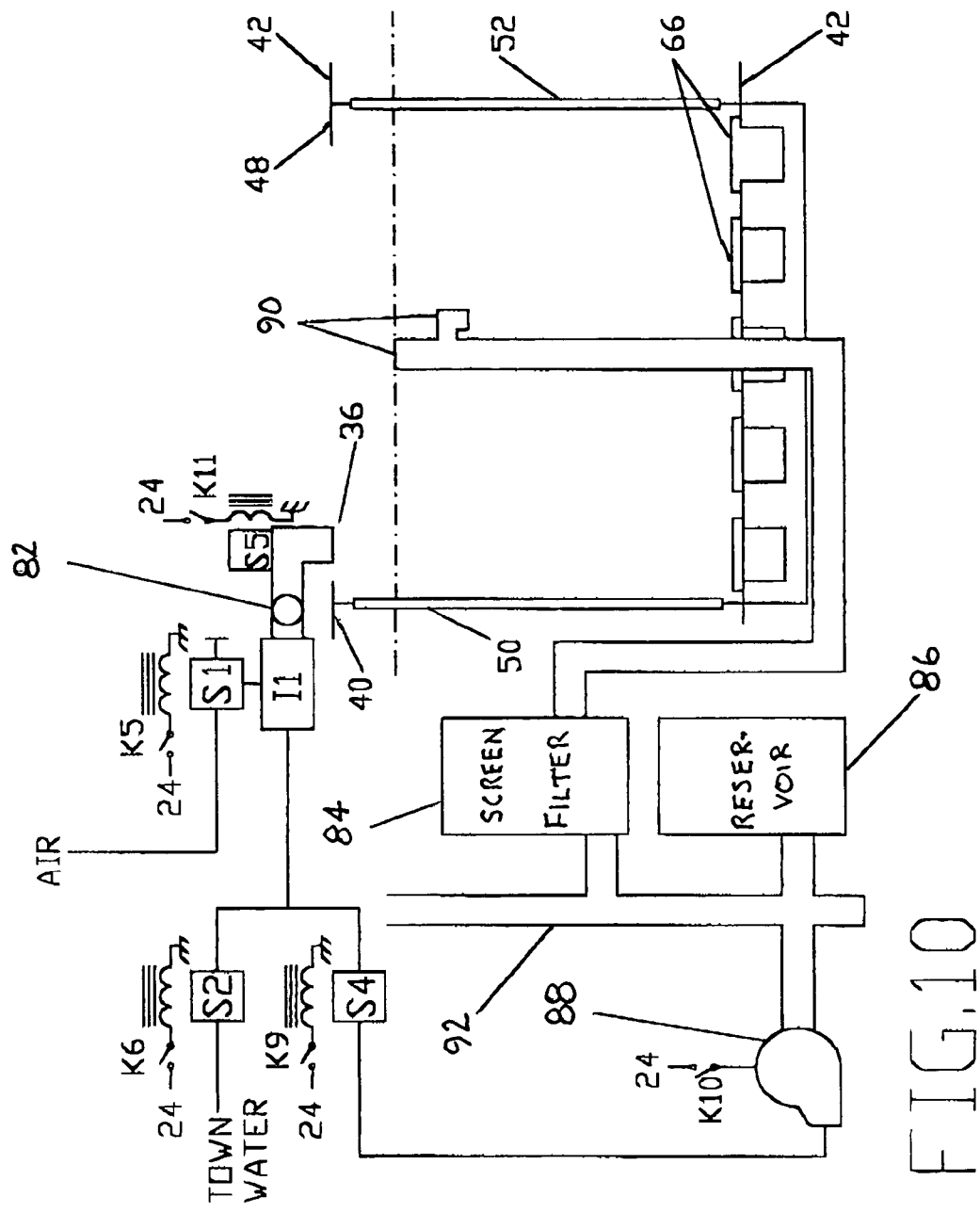
FIG. 10 is partially an electrical circuit diagram and partially a hydraulic circuit diagram of a system for controlling or reducing ammonia levels in fish tank water pursuant to the present invention.

Additionally, FIGS. 4 and 5 illustrate several methods for providing results beneficial for fish raised in fish-farming facilities, for example, the water in which the fish swim can be recirculated continuously and irradiated with high intensity ultrasound for decontamination purposes. In this way waterborne fungi, parasites (e.g., lice) and microorganisms can be destroyed through transient or inertial cavitation without the intervention of disinfectants (without a decontamination cycle).

At selected time periods, daily or two or three times weekly, fish farmed in a system having two or more holding tanks 40, 42 can be recirculated from one tank 40, 42 to another 42, 40 and while passing through an ultrasound section or therapy tank 48 can be irradiated with low intensity ultrasound to effect improvement in blood circulation and fat reduction (wound healing cycle). When used in this manner, ultrasound treatment can be viewed as equivalent to preventative medicine because fish reared in holding tanks are denied vigorous normal "outside activity" which helps to keep them healthy.

Figure 3:
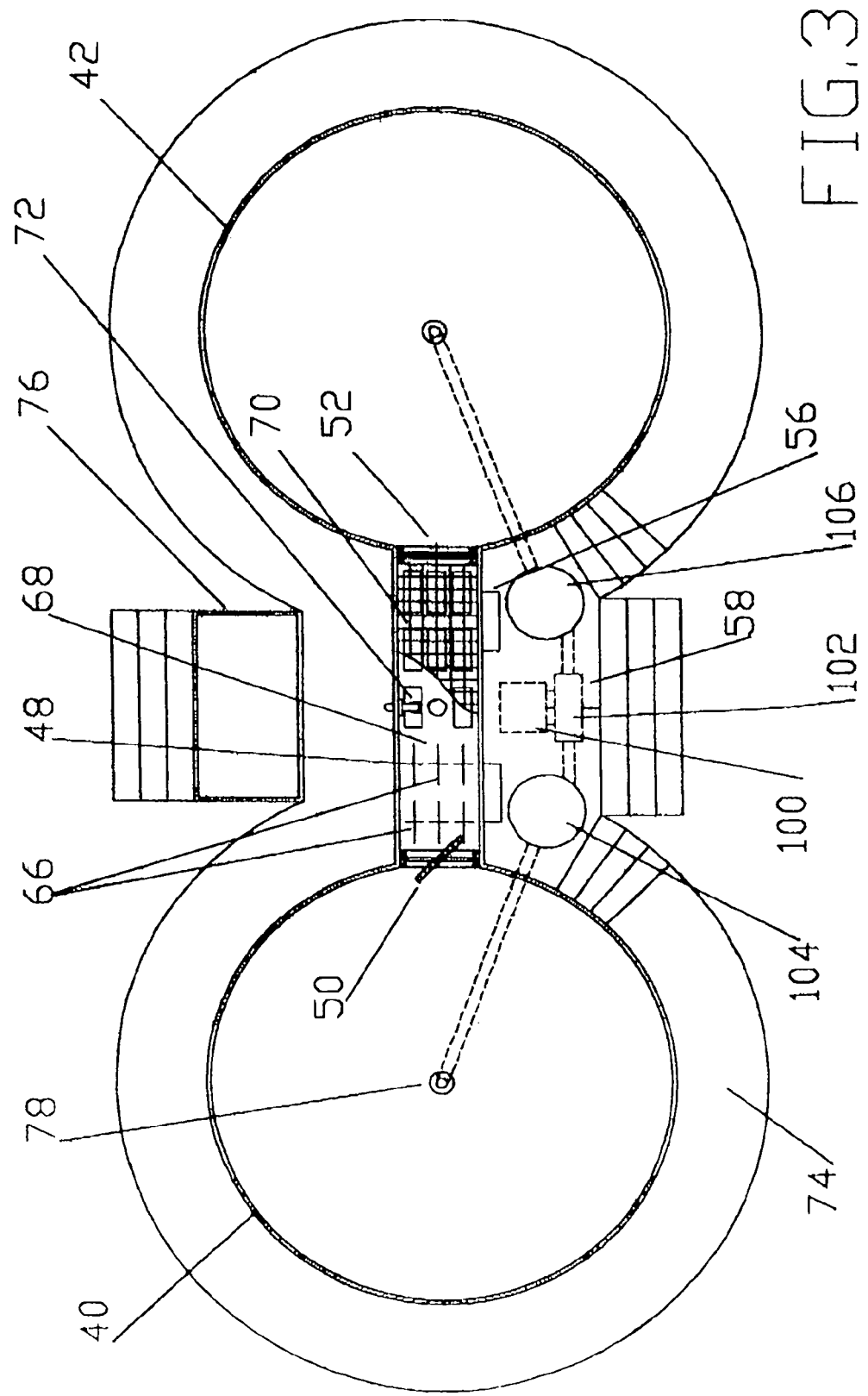
FIG. 3 is a plan view of a two-tank fish farm with an ultrasonic therapy installation in accordance with the present invention.

As depicted in FIG. 3, tank 48 includes a plurality of transducers 66 provided in a bottom surface 68. A tap 72 is provided at an upper end of the tank 48, while a protective mesh or screen 70 may be provided in tank 48 above transducers 66. A walkway 74 is provided about tanks 40, 42, and 48.

Fish in a distressed or contaminated condition can be isolated from healthy fish and treated separately and collectively in the integral ultrasonic therapy tank 48 for removal and destruction of pathogen, fungal and ectoparasitic infection (wound debridement/cleaning cycle). After treatment these fish are isolated by moving them to a separate quarantine tank 76 from which they are periodically ultrasonically treated and not returned until fully cured to the general fish population.

When a two or more holding tank system is in need of maintenance or removal of solid waste excrement from a given tank, then fish can be transferred from one tank 40, 42 to another 42, 40 while this is accomplished. Upon completion, the tank 40, 42 that received maintenance is refilled and the fish transfer accomplished as needed (tank cleaning cycle).

Figure 6:
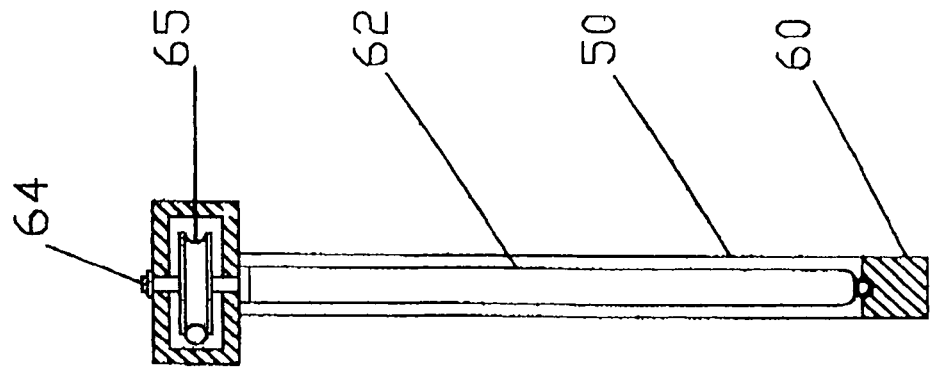
FIG. 6 is a side elevational view of the louvered barrier of FIG. 5.

Louvered barriers 50 and 52 are provided to limit the fish movement between tanks 40, 42 and the ultrasonic therapy tank 48. As depicted in FIGS. 5 and 6, louvered barriers 50 and 52 each include a welded frame 60 and a movable water-sealing louver or door 62 that have a width sufficient to allow free passage of fish. Door 62 is made of a light-weight sound-absorbing material. These louvered barriers 50, 52 can be alternately raised and lowered manually via a lever or knob 64 that turns a worm 63 meshing with a wheel 65. Alternatively and preferably, louvered barriers 50, 52 are operated by automatic means controlled by a microcomputer controller 56. The following description assumes microcomputer automatic control.

As required, a bi-directional circulating motor, pump and filter 58 provide a slow-moving water flow from one tank 40, 42 to another 42, 40. In the decontamination cycle, the louvered barriers 50 and 52 are adjusted sufficiently not to interrupt water-flow but closed sufficiently to prevent fish entry before the high-intensity ultrasound can be activated.

The microcomputer 56 through its LCD requires the operator to remove all fish from the ultrasonic therapy tank 48, which the operator must confirm through appropriate keypad entry. High-intensity ultrasound is then activated to generate transient or inertial cavitation. This operational mode can be sustained 24 hours daily, 7 days weekly or until a different operational cycle is selected using the keypad. However, before such action is undertaken, the microcomputer 56 switches off the high-intensity ultrasound.

As required, the bi-directional motor, pump and filter 58 provide a slow-moving water flow from one tank 40, 42 to another 42, 40. With the wound healing cycle selection, the ultrasonic-tank water tap is activated to provide aerated water into the ultrasonic tank area and remains activated until the fish "conditioning cycle" is completed. When sufficient aeration has been provided, the low-intensity ultrasound is activated and the louvered barriers 50 and 52 are opened fully to permit free fish entry and exit from one tank 40, 42 to another 42, 40. Manual participation of the operator is required to move all fish from one tank to another to ensure that all fish are sonicated.

This fish condition cycle is completed by the operator depressing the stop cycle touchpad. This shuts down the generation of ultrasonic pressure waves in therapy tank 48. The microcomputer 56 through its LCD asks the operator whether all the fish have been removed from the ultrasonic therapy tank, which the operator confirms through appropriate keypad entry. The microcomputer 56 then adjusts louvered barriers 50 and 52 sufficiently not to interrupt water flow but closed sufficiently to prevent fish entry. An adjustable automatic timer (part of the microcomputer 56) is provided to automatically shut down this cycle in the event of operator absence.

As required, the bi-directional motor, pump and filter 58 must be switched off and the louvered barriers 50 and 52 tightly closed by a pneumatic pump 80 that inflates a tubular sealing member 81. The operator depresses the microcomputer stop cycle touchpad to accomplish this. The LCD will ask the operator "what's next." The operator uses the sequencer touchpad 22 (FIG. 1) to select and then start the wound debridement/cleaning cycle. This cycle is almost identical to that used for humans, except that the microcomputer 56 simultaneously fills and drains the ultrasonic therapy tank 48 until the necessary aerated water exchange is effectuated after which a drain 54 is closed and the ultrasonics switched on. The distressed or contaminated fish are placed in the therapy tank 48 for the automatically prescribed treatment time period. Thereafter the microcomputer LCD instructs the operator to remove the fish to quarantine tank 76 and requires confirmation from the operator. This treatment cycle is to be repeated periodically every few days until the fish(es) in question is judged healed and free from infection.

Following the current fish decontamination cycle, the operator uses the touchpad to initiate a high ultrasound intensity decontamination cycle in therapy tank 48, after which the microcomputer 56 switches off the ultrasound and drains the tank. After tank draining, the microcomputer asks the operator if the debridement/cleaning cycle is to be repeated. If the answer is in the affirmative, the microcomputer 56 refills the tank, etc., and proceeds as before. If not, the microcomputer 56 adjusts louvered barriers 50 and 52 sufficiently not to interrupt water flow but closed sufficiently to prevent fish entry. In debridement/cleaning cycle, it is to be noted that with every therapy tank emptying the opening of louvered barriers 50 and 52 will lower the water level in the fish holding tanks 40 and 42. This level depletion will be automatically made up by automatic water level sensing floats (not shown).

At the next operator cycle selection, other than debridement/cleaning cycle, the microcomputer 56 will switch the water circulating motor, pump and filter 58 back on.

In the event that solid excrement waste from the fish tank needs to be removed from a holding tank, the following procedure is performed. The operator, using the touchpad sequencer, selects "excrement removal, Tank B" (referring to tank 42), for example, and starts the process. The microcomputer 56 fully opens louvered barriers 50 and 52 to allow free passage of the fish and subsequently reverses the flow of the recirculating pump to assist in fish transfer from tank 42 to tank 40. After all the fish have been transferred then the operator, using the touchpad, alerts the microcomputer 56 which then fully closes barrier 50 while barrier 52 is left open and the circulating pump is again reversed which empties tank 42 to "drain" after which the circulating pump is switched off.

After excrement removal, tank 42 is refilled, barrier 50 is opened and the microcomputer 56 switches the circulating pump back on, allowing the fish to return with assistance from tank 40 to tank 42, for example.

As part of the water high intensity ultrasound decontamination cycle the microcomputer 56 automatically reverses the water flow commensurate with time necessary to drain the holding tank in question.

In inertial or transient cavitation, the time from individual bubble inception to implosion within the amorphous water mass contained in treatment tank 26 is variable. The mechanism for this variability is the local positive to negative excursion of pressure amplitude around a point of bubble inception-sensitivity.

The formula that links intensity (an area expression) and pressure is $I=p^2/\rho c$, where I is the intensity in acoustic watts per cm$^2$, p is the pressure amplitude in Pascals (in the plane of measurement), and $\rho c$ is the acoustic impedance of water.

The location of a particular intensity and pressure relationship within the therapy tank 26 will depend on the location of the ultrasound transducer T1 within the geometry of the tank volume. Throughout the tank 26, the local value of intensity and therefore pressure amplitude will vary due to the uneven ultrasound pressure propagation characteristics emanating from the face of the transducer T1 and, to a much lesser extent, to the pressure amplitude attenuation characteristics of the water mass.

It follows that pressure amplitude will vary with the distance of the propagated ultrasound wave front from the transducer T1 and will also vary within the area of a given transverse plane. In general, pressure amplitude excursion and associated intensity will decrease the further the pressure measurement plane is from the transducer face plate.

In practice, over the relatively short distances involved within a small volume therapy tank 26, it is anticipated that by setting the required PRP/Intensity value local to the plane of the transducer T1 will serve to effect the necessary elimination of transient cavitation throughout the therapy tank and thereby promote the necessary level of microstreaming activity.

However, when using larger therapy tanks where the patient is in a supine position with feet in relative close proximity to the transducer, a PRP/Intensity setting suitable for lower extremity microstreaming therapy treatment may not induce sufficient microstreaming for upper extremity treatment. This situation, for example, would require an increase in transducer intensity and proportional decrease in PRP to eliminate the possibility of transient cavitation around the lower extremities while promoting the necessary level of microstreaming around the upper extremities.

This indicates that for one patient therapy treatment cycle it will be necessary to employ at least two intensity (pressure amplitude levels). Thus, pressure amplitude (intensity) and PRP must vary during an ultrasound session. There are many other situations during a therapy cycle where intensity (pressure amplitude) settings must be automatically compensated for such as electrical voltage power fluctuations, for example. In brief, where it is necessary to adjust intensity or applied ultrasound waves by adjusting the amplitude of the electrical signal energizing the transducer, the microprocessor 24 will automatically vary or change the PRP in inverse relationship to the adjustment in intensity or amplitude, to ensure that inertial or transient cavitation is avoided. The microprocessor 24 controls the amplitude of the alternating electrical signal energizing the transducer, thereby determining the intensity of the ultrasonic pressure waves produced in the tank by the transducer. The microprocessor controller 24 also varies the pulse repetition period of the electrical signal in inverse relationship to variation of the amplitude.

It should be understood that the apparatus and method of the present disclosure ensure that transient cavitation is always suppressed, while stable cavitation is automatically maintained. Initial site calibration automatic may be automatic. Routine operation may be fully automatic and analogous to a servo-loop where PZT probe or detector X1 provides an error signal for the onset of cavitation, causing the microprocessor 24 to apply half-wave rectification which re-establishes stable cavitation and resets full-wave to half-wave parameters and subsequently transitions from full-wave to half-wave earlier on in the pulse transmission, to provide a safety margin.

FIG. 7 is a graph of bubble radius vs. time, illustrating stable cavitation degenerating into transient cavitation. FIG. 8 is a graph similar to FIG. 7 and depicts an interval of stable cavitation followed by a period of rectified half-wave transmission. When PZT probe X1 detects an onset of transient cavitation, it signals microprocessor 24 to initiate half-wave transmission, which occurs in FIG. 8 at a transition from full-wave to half-wave transmission. Subsequently, as shown in FIG. 9, microprocessor 24 terminates half-wave rectification and resumes full-wave transmission, cyclically as programmed.

A fish tank installation with ultrasonic wound debridement and healing therapy as discussed above may additionally be provided with a system for reducing ammonia concentrations caused by the presence of fish faeces and un-eaten fish feed particulate matter in recirculating aquaculture tanks 40 and 42. Sensors (not shown) may be inserted into the water in tanks 40 and 42 to monitor the levels of ammonia and carbon dioxide therein. The sensors may be connected displays and/ or other communication devices such as audio alarms for alerting caretaker personnel of the need for ammonia removal.

The first action of microprocessor 24 upon initiation of an ultrasonic ammonia neutralization process is to close the louvered barriers 50 and 52 and energize a solenoid S5 to close branch piping 82, and open faucet or elbow pipe 36. At this point the operator must remove any stray fish from tank 48 and deposit them into either tank 40 or 42, as appropriate. Thus, a portion of the total tank water is isolated in tank 48 for ammonia neutralization and carbon dioxide removal.

After stray fish removal, the operator, through microprocessor 24, activates the transducers 66 for a predetermined time period sufficient to detoxify ammonia and carbon-dioxide from the isolated volume of water contained by tank 48 and also the liquid contained by a contiguous screen filter 84, a reservoir 86, and extraneous piping. After the detoxification time period has elapsed, microprocessor 24 deactivates the transducers 66, opens the louvered barriers 50 and 52 and de-energizes solenoid S5 to open the branch piping 82 and close faucet 36.

Subsequent to the neutralization or removal or ammonia and carbon dioxide via the generation of transient cavitation bubbles through ultrasonic pressure waves, microprocessor 24 (or the operator) initiates a process for the removal of particulate matter and oxygenation. A circulating pump 88 is activated to suck liquid from the tank 48 via a central standpipe 90, through the screen filter 84, which restrains further passage of larger particulate matter, then to distribute or pass the filtered liquid down through an atmospheric standpipe 92, by-passing the reservoir 86, through the low pressure entry in circulating pump 88, through a solenoid S4 into the branch piping 82, and finally through air venturi I1 into tanks 40 and 42.

Figure 11:
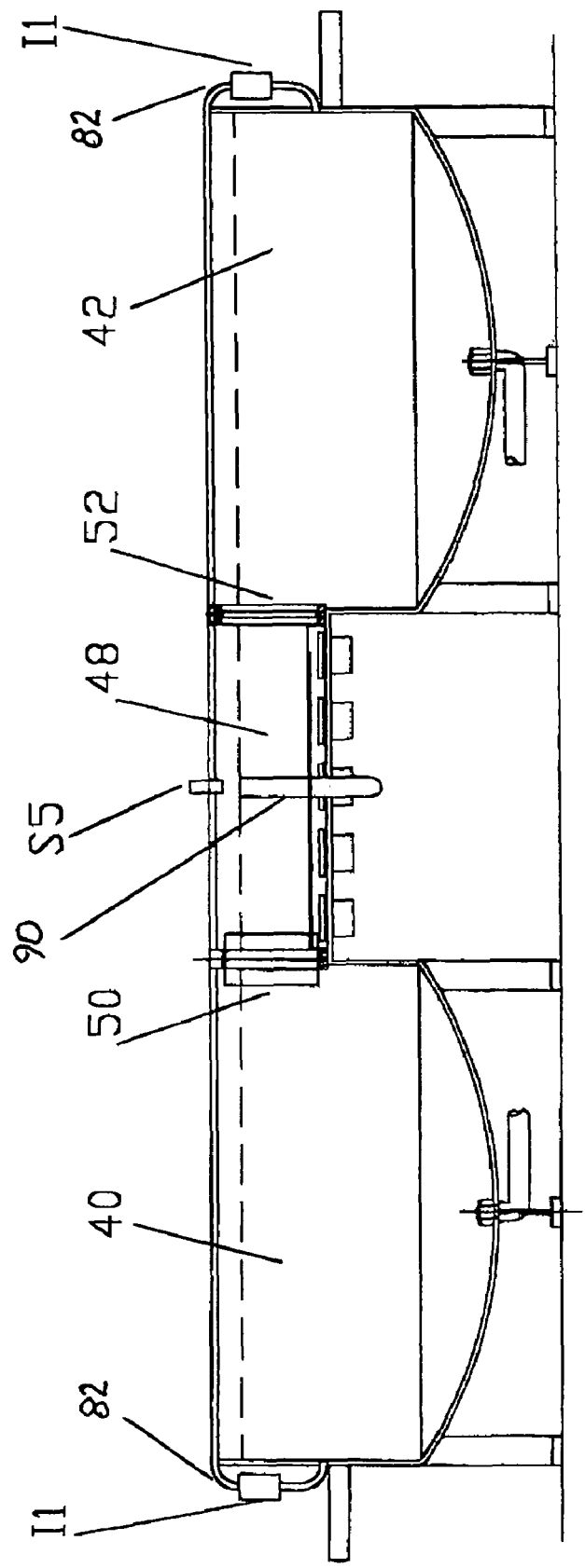
FIG. 11 is a schematic side elevational view of a two-tank fish farm with the system of FIG. 10.

As illustrated in FIG. 11, the filtered liquid from the branch piping 82 re-enters tanks 40 and 42 at the furthermost distance from central standpipe 90. Aerating the liquid at these furthermost locations provides for vigorous stirring action of the contents of tanks 40 and 42 and drives the liquid containing un-eaten fish feed particulate matter towards the central standpipe 90 for acquisition and filtering.

This continuous recirculation process of filtered oxygenated liquid continues until next interrupted by microprocessor 24, for the aforementioned need for ammonia and carbon-dioxide detoxification cycle.

Solenoids S2 and S4 are placed in parallel so that in extenuating circumstances temporary open-loop operation can be employed.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and description herein are proffered by way of example to facilitate comprehension of the invention and should not be construed to limit the scope thereof.

What is claimed is:

1. An ultrasonic treatment method comprising:
   feeding water to a tank;
   introducing air in said water;
   disposing a living fish in the aerated water;
   thereafter ultrasonically generating stable vibrating bubbles in said aerated water, the generating of said stable vibrating bubbles including energizing a transducer with first full-wave compression and rarefaction cycles, said first full-wave compression and rarefaction cycles having a first amplitude or intensity and a first pulse repetition period;
   automatically monitoring the aerated water in said tank to detect an onset of inertial or transient cavitation; and
   subsequently at the detection of the onset of inertial or transient cavitation energizing said transducer with rectified-wave compression pressure cycles, so as to suppress inertial or transient cavitation.

2. The method defined in claim 1, further comprising displaying a status of inertial of transient cavitation in the aerated water in said tank.

3. The method defined in claim 1, further comprising:
   removing the fish from said tank;
   thereafter delivering disinfectant and water to said tank; and
   thereafter inducing ultrasonic transient cavitation in the water and disinfectant in said tank.

4. The method defined in claim 1, further comprising subsequently energizing said transducer with periods of second full-wave compression and rarefaction cycles alternating with periods of second rectified-wave compression pressure cycles, said second full-wave compression and rarefaction cycles having a second amplitude or intensity greater or less than said first amplitude or intensity and a second pulse repetition period respectively less or greater than said first pulse repetition period and said second rectified-wave compression pressure cycles having said second amplitude or intensity and said second pulse repetition period so that said second full-wave compression and rarefaction cycles alternate with periods of said second rectified-wave compression pressure cycles.

5. The method defined in claim 4, wherein said second pulse repetition period differs from said first pulse repetition period in inverse relationship to a variation of said second amplitude relative to said first amplitude.

* * * * *